US00PP18765P2

(12) United States Plant Patent
Masopust

(10) Patent No.: US PP18,765 P2
(45) Date of Patent: Apr. 29, 2008

(54) *CHRYSANTHEMUM* PLANT NAMED 'SPARKLING YOCHERYL'

(50) Latin Name: *Chrysanthemum×morifolium*
Varietal Denomination: Sparkling Yocheryl

(75) Inventor: Daniel Masopust, Morris, CT (US)

(73) Assignee: Yoder Brothers Inc., Barberton, OH (US)

( * ) Notice: Subject to any disclaimer, the term of this patent is extended or adjusted under 35 U.S.C. 154(b) by 0 days.

(21) Appl. No.: 11/648,870

(22) Filed: Dec. 29, 2006

(51) Int. Cl.
*A01H 5/00* (2006.01)

(52) U.S. Cl. ..... Plt./289

(58) Field of Classification Search ..... Plt./289
See application file for complete search history.

*Primary Examiner*—Kent Bell
(74) *Attorney, Agent, or Firm*—C. A. Whealy

(57) ABSTRACT

A new and distinct cultivar of *Chrysanthemum* plant named 'Sparkling Yocheryl', characterized by its compact, upright and outwardly spreading plant habit; freely branching habit; dense and full plant habit; uniform and freely flowering habit; decorative-type inflorescences with elongated oblong to ligulate-shaped ray florets; yellow-colored ray florets; and natural season flowering about October 5$^{th}$ in the Northern Hemisphere.

1 Drawing Sheet

Botanical designation: *Chrysanthemum×morifolium.*
Cultivar denomination: 'Sparkling Yocheryl'.

BACKGROUND OF THE INVENTION

The present invention relates to a new and distinct cultivar of *Chrysanthemum* plant, botanically known as *Chrysanthemum×morifolium,* commercially grown as a garden *Chrysanthemum* and hereinafter referred to by the name 'Sparkling Yocheryl'.

The new *Chrysanthemum* is a naturally-occurring whole plant mutation of the *Chrysanthemum×morifolium* cultivar Golden Yocheryl, disclosed in U.S. Plant Pat. No. 16,383. The new *Chrysanthemum* was discovered and selected by the Inventor as a single flowering plant within a population of plants of the parent cultivar in October, 2004, in Morris, Connecticut. The selection of this plant was based on its desirable inflorescence color and good form and substance.

Asexual reproduction of the new *Chrysanthemum* by vegetative cuttings was first conducted in Gainesville, Fla. in March, 2005. Asexual reproduction by cuttings has shown that the unique features of this new *Chrysanthemum* are stable and reproduced true to type in successive generations.

SUMMARY OF THE INVENTION

Plants of the cultivar Sparkling Yocheryl have not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Sparkling Yocheryl'. These characteristics in combination distinguish 'Sparkling Yocheryl' as a new and distinct garden *Chrysanthemum* cultivar:

1. Compact, upright and outwardly spreading plant habit.
2. Freely branching habit; dense and full plant habit.
3. Uniform and freely flowering habit.

4. Decorative-type inflorescences with elongated oblong to ligulate-shaped ray florets.
5. Yellow-colored ray florets.
6. Natural season flowering about October 5$^{th}$ in the Northern Hemisphere.

In side-by-side comparisons conducted in Alva, Fla. plants of the new *Chrysanthemum* differed from plants of the parent, the cultivar Golden Yocheryl, in the following characteristics:

1. Plants of the new *Chrysanthemum* were slightly smaller than plants of 'Golden Yocheryl'.
2. Plants of the new *Chrysanthemum* and the cultivar Golden Yocheryl differed in ray floret coloration.

Plants of the new *Chrysanthemum* can be compared to plants of the *Chrysanthemum* cultivar Yoerica, disclosed in U.S. Plant Pat. No. 11,842. In side-by-side comparisons conducted in Alva, Fla. plants of the new *Chrysanthemum* differed from plants of the cultivar Yoerica in the following characteristics:

1. Plants of the new *Chrysanthemum* had darker green-colored leaves than plants of the cultivar Yoerica.
2. Plants of the new *Chrysanthemum* flowered later than plants of the cultivar Yoerica.

BRIEF DESCRIPTION OF THE PHOTOGRAPHS

The accompanying photographs illustrate the overall appearance of the new *Chrysanthemum.* These photographs show the colors as true as it is reasonably possible to obtain in colored reproductions of this type. Colors in the photographs may differ slightly from the color values cited in the detailed botanical description which accurately describe the colors of the new *Chrysanthemum.*

The photograph at the bottom of the sheet comprises a side perspective view of a typical flowering plant of 'Sparkling Yocheryl'.

The photograph at the top of the sheet is a close-up view of typical inflorescences of 'Sparkling Yocheryl'.

DETAILED BOTANICAL DESCRIPTION

The aforementioned photographs and following observations and measurements describe plants grown in Fletcher, N.C. during the summer in an outdoor nursery and under conditions and practices which approximate those generally used in commercial garden *Chrysanthemum* production. During the production of the plants, day temperatures averaged 29° C. and night temperatures averaged 16° C. Plants were grown in 15-cm containers, exposed to long day/short night conditions and pinched about two weeks later. About two weeks after the pinch, the photoinductive short day/long night treatments were started. Plants used in the photographs and for the description were about three months old. In the following description, color references are made to The Royal Horticultural Society Colour Chart, 1995 Edition, except where general terms of ordinary dictionary significance are used.

Botanical classification: *Chrysanthemum×morifolium* cultivar Sparkling Yocheryl.

Parentage:

Naturally-occurring whole plant mutation of the *Chrysanthemum×morifolium* cultivar Golden Yocheryl, disclosed in U.S. Plant Pat. No. 16,383.

Propagation:

*Type.*—Terminal vegetative cuttings.

*Time to initiate roots.*—About four days at temperatures of about 21° C.

*Time to produce a rooted young plant.*—About ten to twelve days at temperatures of about 21° C.

*Root description.*—Fine, fibrous; white in color.

*Rooting habit.*—Freely branching.

Plant description:

*Appearance.*—Herbaceous decorative-type garden *Chrysanthemum.* Stems upright and outwardly spreading giving a uniformly mounded appearance to the plant. Freely branching habit, about six lateral branches develop after removal of terminal apex (pinching) each with numerous secondary laterals; dense and full plant habit. Strong and vigorous growth habit.

*Plant height.*—About 19.5 cm.

*Plant width.*—About 26 cm.

*Lateral branches.*—Length: About 19 cm. Diameter: About 6 mm. Internode length: About 9 mm. Strength: Strong. Texture: Pubescent. Color: 144A.

*Leaves.*—Arrangement: Alternate, simple. Length: About 5.6 cm. Width: About 3.6 cm. Apex: Broadly acute. Base: Attenuate. Margin: Palmately lobed, sinuses between lateral lobes mostly divergent. Texture, upper and lower surfaces: Fine pubescence; veins prominent on lower surface. Color: Developing foliage, upper and lower surfaces: 147A. Fully expanded foliage, upper surface: 147A; venation, 147B. Fully expanded foliage, lower surface: 147B; venation, 147B. Petiole: Length: About 1.5 cm. Diameter: About 2 mm. Texture, upper and lower surfaces: Pubescent. Color, upper surface: 147A. Color, lower surface: 147B.

Inflorescence description:

*Appearance.*—Decorative-type inflorescence form with elongated oblong to ligulate-shaped ray florets. Inflorescences borne on terminals above foliage. Disk and ray florets arranged acropetally on a capitulum. Inflorescences faintly fragrant.

*Flowering response.*—Under natural season conditions, plants flower about October 5$^{th}$ in the Northern Hemisphere. At other times of the year, inflorescence initiation and development can be induced under short day/long night conditions (at least 13.5 hours of darkness). Early flowering habit; plants exposed to photoinductive short day/long night conditions flower about 51 days later.

*Postproduction longevity.*—Inflorescences maintain good color and substance for about four weeks in an outdoor nursery.

*Quantity of inflorescences.*—About 17 to 19 inflorescences develop per lateral branch.

*Inflorescence bud.*—Height: About 1.2 cm. Diameter: About 1 cm. Shape: Ovoid. Color: 5A.

*Inflorescence size.*—Diameter: About 4.5 cm. Depth (height): About 3 cm. Disc diameter: About 3 mm; inconspicuous. Receptacle diameter: About 1.6 cm. Receptacle height: About 4 mm.

*Ray florets.*—Shape: Elongated-oblong to ligulate. Orientation: Initially upright, then about 90° from vertical or perpendicular to peduncle. Aspect: Initially incurved, then mostly flat with development. Length: About 2.1 cm. Width: About 7 mm. Apex: Rounded. Base: Acute. Margin: Entire. Texture, upper and lower surfaces: Smooth, glabrous, satiny. Number of ray florets per inflorescence: About 287 arranged in about 14 whorls. Color: When opening and fully opened, upper surface: 8A. When opening and fully opened, lower surface: 6D.

*Disc florets.*—Shape: Tubular, elongated. Length: About 2.5 mm. Diameter: About 1 mm. Number of disc florets per inflorescence: About 22. Color, immature and mature: Apex: Close to 14C. Midsection: Close to 11C. Base: Close to 157D.

*Phyllaries.*—Number of phyllaries per inflorescence: About 34 arranged in about two to three whorls. Length: About 6 mm. Width: About 3 mm. Shape: Elliptical. Apex: Acute. Base: Truncate. Texture, upper surface: Smooth, waxy. Texture, lower surface: Pubescent. Color, upper and lower surfaces: Close to 148A.

*Peduncles.*—Length: About 3.3 cm. Diameter: About 2.5 mm. Angle: About 45° from vertical. Strength: Strong. Texture: Pubescent; longitudinally ridged. Color: Close to 148A.

*Reproductive organs.*—Androecium: None observed. Gynoecium: Pistil length: About 4 mm. Stigma shape: Bi-parted. Stigma color: Close to 10B. Style length: About 2 mm. Style color: Close to 10D. Ovary color: Close to 145B.

*Seed/fruit.*—Seed and fruit production has not been observed.

Disease/pest resistance: Resistance to pathogens and pests common to *Chrysanthemums* has not been observed on plants grown under commercial conditions.

Garden performance: Plants of the new *Chrysanthemum* have demonstrated excellent garden performance and to tolerate temperatures from about 0° C. to about 38° C.

It is claimed:

1. A new and distinct *Chrysanthemum* plant named 'Sparkling Yocheryl' as illustrated and described.

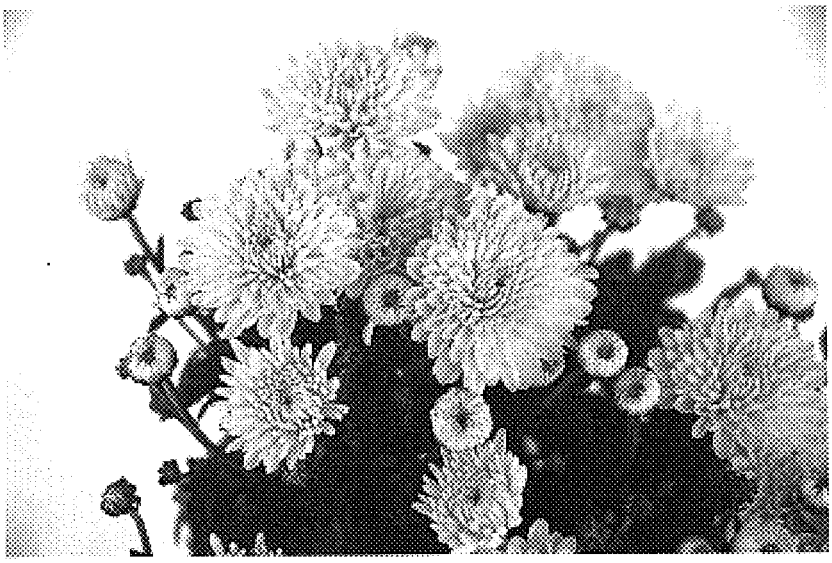
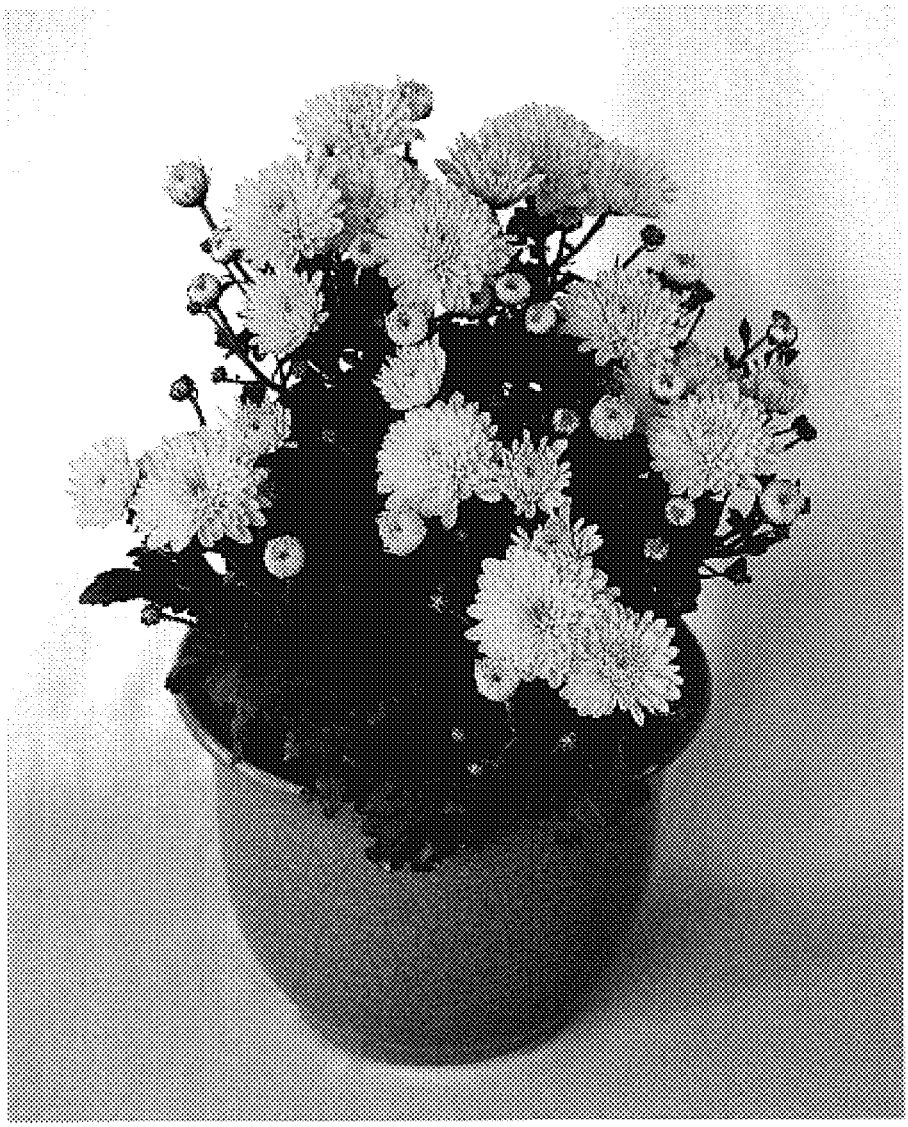

* * * * *